(12) United States Patent
Lan et al.

(10) Patent No.: US 8,202,974 B2
(45) Date of Patent: Jun. 19, 2012

(54) SYNTHETIC RNA-BASED AGONISTS OF TLR7

(75) Inventors: Tao Lan, Arlington, MA (US); Ekambar Kandimalla, Southboro, MA (US); Daqing Wang, Bedford, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/703,612

(22) Filed: Feb. 10, 2010

(65) Prior Publication Data

US 2010/0215642 A1     Aug. 26, 2010

Related U.S. Application Data

(60) Provisional application No. 61/151,211, filed on Feb. 10, 2009.

(51) Int. Cl.
| | | |
|---|---|---|
| *C07H 21/02* | (2006.01) | |
| *C07H 21/04* | (2006.01) | |
| *C12Q 1/68* | (2006.01) | |
| *C12N 5/00* | (2006.01) | |
| *C12N 5/02* | (2006.01) | |
| *A61K 49/00* | (2006.01) | |
| *A61K 31/70* | (2006.01) | |
| *A01N 43/04* | (2006.01) | |

(52) U.S. Cl. ......... 536/23.1; 435/6.1; 435/375; 424/9.2; 514/44 R

(58) Field of Classification Search .................. None
See application file for complete search history.

(56) References Cited

U.S. PATENT DOCUMENTS

| | | | | |
|---|---|---|---|---|
| 6,150,092 | A | * 11/2000 | Uchida et al. | 536/24.5 |
| 2005/0130918 | A1 | * 6/2005 | Agrawal et al. | 514/44 |
| 2006/0241076 | A1 | * 10/2006 | Uhlmann et al. | 514/44 |

FOREIGN PATENT DOCUMENTS

| | | | |
|---|---|---|---|
| WO | WO 2007048046 | A2 * | 4/2007 |
| WO | WO 2008109558 | A2 * | 9/2008 |
| WO | WO 2009014887 | A2 * | 1/2009 |

* cited by examiner

*Primary Examiner* — Dana Shin
(74) *Attorney, Agent, or Firm* — Wood, Phillips, Katz, Clark & Mortimer

(57) ABSTRACT

The invention relates to the therapeutic use of stabilized oligoribonucleotides as immune modulatory agents for immune therapy applications. Specifically, the invention provides RNA-based oligoribonucleotides with improved nuclease and RNase stability and that selectively induce immune modulatory activity through TLR7.

3 Claims, 1 Drawing Sheet

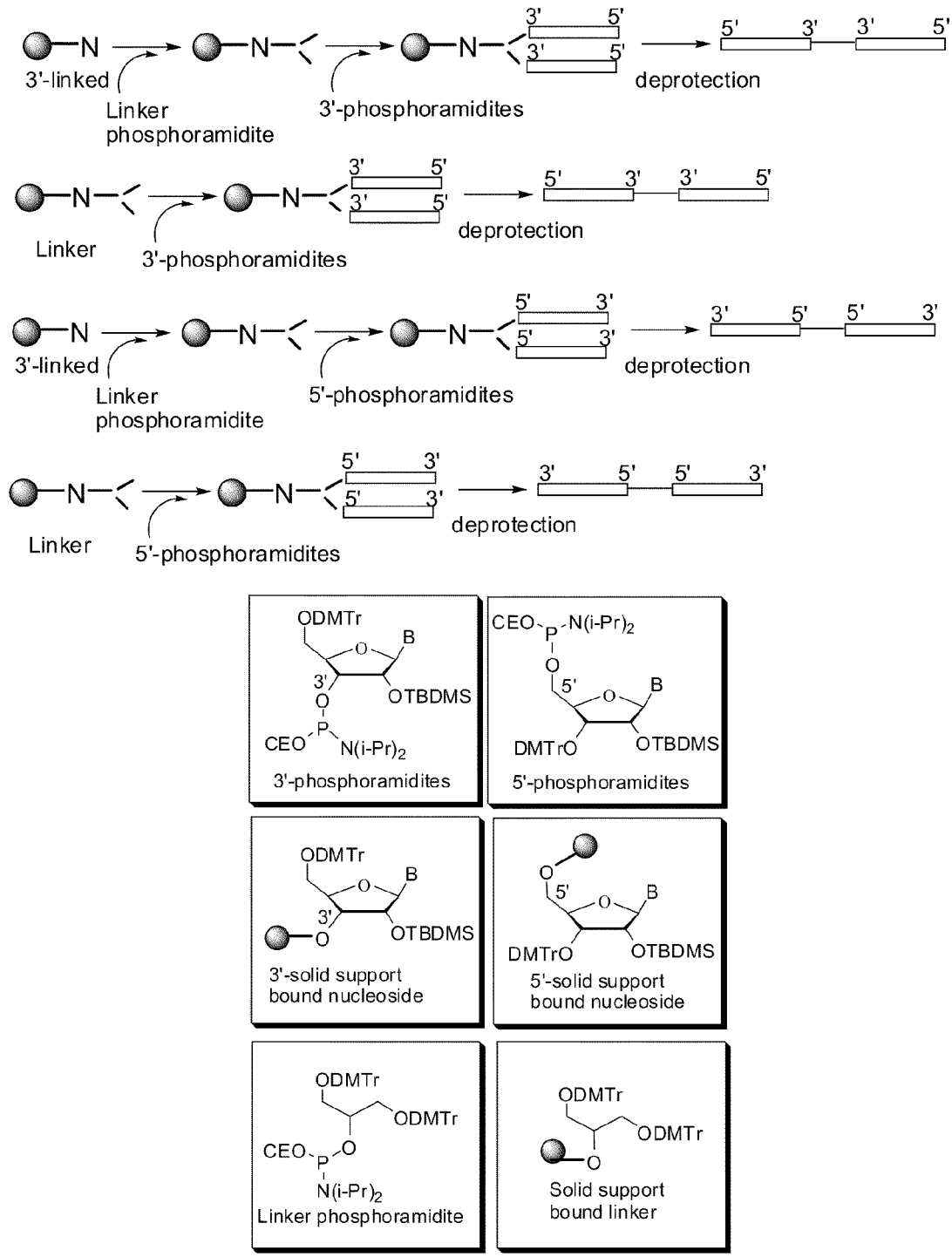

SEQUENCE LISTING

<160> NUMBER OF SEQ ID NOS: 31

<210> SEQ ID NO 1
<211> LENGTH: 11
<212> TYPE: RNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 1
uugcugagcu u                                                              11

<210> SEQ ID NO 2
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 2
ugaugacgau u                                                              11

<210> SEQ ID NO 3
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 3
ugacgaugau u                                                              11

<210> SEQ ID NO 4
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 7-deaza-guanosine
<220> FEATURE:
<221> NAME/KEY: misc_feature
```

```
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 4
cuugugagcu u                                                              11

<210> SEQ ID NO 5
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 5
cugagaagcu u                                                              11

<210> SEQ ID NO 6
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 6
cugacgagcu u                                                              11

<210> SEQ ID NO 7
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (10)..(10)
<223> OTHER INFORMATION: 7-deaza-guanosine

<400> SEQUENCE: 7
acuugacuug a                                                              11
```

```
<210> SEQ ID NO 8
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 8
acuugacgau u                                                           11

<210> SEQ ID NO 9
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine

<400> SEQUENCE: 9
acuugaccuu u                                                           11

<210> SEQ ID NO 10
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (10)..(10)
<223> OTHER INFORMATION: 7-deaza-guanosine

<400> SEQUENCE: 10
acuugaccug u                                                           11

<210> SEQ ID NO 11
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 11
acuugaagcu u                                                           11

<210> SEQ ID NO 12
<211> LENGTH: 11
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (11)..(11)
<223> OTHER INFORMATION: 7-deaza-guanosine

<400> SEQUENCE: 12
acuugaacuu g                                                            11

<210> SEQ ID NO 13
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine

<400> SEQUENCE: 13
acuugaaacc u                                                            11

<210> SEQ ID NO 14
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 7-deaza-guanosine
<220> FEATURE:
<221> NAME/KEY: misc_feature
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 14
acugcgagcu u                                                            11

<210> SEQ ID NO 15
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 7-deaza-guanosine
<220> FEATURE:
<221> NAME/KEY: misc_feature
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 15
acugagagcu u                                                            11
```

```
<210> SEQ ID NO 16
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 16
acgugaagcu u                                                          11

<210> SEQ ID NO 17
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 17
acgcugagcu u                                                          11

<210> SEQ ID NO 18
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 18
aauugacgcu u                                                          11

<210> SEQ ID NO 19
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
```

```
<222> LOCATION: (8)..(8)
<223> OTHER INFORMATION: 7-deaza-guanosine
<220> FEATURE:
<221> NAME/KEY: misc_feature
<222> LOCATION: (11)..(11)
<223> OTHER INFORMATION: 7-deaza-guanosine

<400> SEQUENCE: 19
aauugacgcu g                                                          11

<210> SEQ ID NO 20
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (7)..(7)
<223> OTHER INFORMATION: 7-deaza-guanosine

<400> SEQUENCE: 20
aagugcgacu u                                                          11

<210> SEQ ID NO 21
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 21
aagugacgcu u                                                          11

<210> SEQ ID NO 22
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 22
```
aagugacgau u                                                                 11

<210> SEQ ID NO 23
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 23
aacuugagcu u                                                                 11

<210> SEQ ID NO 24
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (7)..(7)
<223> OTHER INFORMATION: 7-deaza-guanosine

<400> SEQUENCE: 24
aacugcgacu u                                                                 11

<210> SEQ ID NO 25
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 25
aacugacgcu u                                                                 11

<210> SEQ ID NO 26
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine
<220> FEATURE:
<221> NAME/KEY: misc_feature

```
<222> LOCATION: (11)..(11)
<223> OTHER INFORMATION: 7-deaza-guanosine

<400> SEQUENCE: 26
aacugacgcu g                                                              11

<210> SEQ ID NO 27
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 7-deaza-guanosine
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 27
ugaugaagcu u                                                              11

<210> SEQ ID NO 28
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 28
aacugaagcu u                                                              11

<210> SEQ ID NO 29
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine
<220> FEATURE:
<221> NAME/KEY: misc_feature
<222> LOCATION: (11)..(11)
<223> OTHER INFORMATION: 7-deaza-guanosine

<400> SEQUENCE: 29
aacugaagcu g                                                              11

<210> SEQ ID NO 30
<211> LENGTH: 11
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine

<400> SEQUENCE: 30
aauugaagcu u                                                          11

<210> SEQ ID NO 31
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 7-deaza-guanosine
<220> FEATURE:
<221> NAME/KEY: misc_feature
<222> LOCATION: (8)..(8)
<223> OTHER INFORMATION: 7-deaza-guanosine
<220> FEATURE:
<221> NAME/KEY: misc_feature
<222> LOCATION: (11)..(11)
<223> OTHER INFORMATION: 7-deaza-guanosine

<400> SEQUENCE: 31
aauugaagcu g                                                          11
```

SYNTHETIC RNA-BASED AGONISTS OF TLR7

This application claims the benefit of priority from U.S. Provisional Patent Application No. 61/151,211, filed on Feb. 10, 2009, the disclosure of which is explicitly incorporated by reference herein.

BACKGROUND OF THE INVENTION

1. Field of the Invention

The invention relates generally to the field of immunology and immunotherapy applications using oligoribonucleotides as immune modulatory agents. More particularly, the invention relates to immune modulatory RNA compositions and methods of use thereof for modulating the immune response through Toll-like receptor 7 (TLR7).

2. Summary of the Related Art

The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells, whereas the Th cells involved as helper cells for B-cell activation are Th2 cells. The type of immune response is influenced by the cytokines and chemokines produced in response to antigen exposure. Cytokines provide a means for controlling the immune response by affecting the balance of T helper 1 (Th1) and T helper 2 (Th2) cells, which directly affects the type of immune response that occurs. If the balance is toward higher numbers of Th1 cells, then a cell-mediated immune response occurs, which includes activation of cytotoxic T cells (CTLs). When the balance is toward higher numbers of Th2 cells, then a humoral or antibody immune response occurs. Each of these immune response results in a different set of cytokines being secreted from Th1 and Th2 cells. Differences in the cytokines secreted by Th1 and Th2 cells may be the result of the different biological functions of these two T cell subsets.

Th1 cells are involved in the body's innate response to antigens (e.g., viral infections, intracellular pathogens, and tumor cells). The initial response to an antigen can be the secretion of IL-12 from antigen presenting cells (e.g., activated macrophages and dendritic cells) and the concomitant activation of Th1 cells. The result of activating Th1 cells is a secretion of certain cytokines (e.g., IL-2, IFN-gamma and other cytokines) and a concomitant activation of antigen-specific CTLs. Th2 cells are known to be activated in response to bacteria, parasites, antigens, and allergens and may mediate the body's adaptive immune response (e.g., immunoglobulin production and eosinophil activation) through the secretion of certain cytokines (e.g., IL-3, IL-4, IL-5, IL-6, IL-9, IL-10, IL-13 and other cytokines) and chemokines Secretion of certain of these cytokines may result in B-cell proliferation and an increase in antibody production. In addition, certain of these cytokines may stimulate or inhibit the release of other cytokines (e.g., IL-10 inhibits IFN-γ secretion from Th1 cells and IL-12 from dendritic cells). Ultimately, the balance between Th1 and Th2 cells and the cytokines and chemokines released in response to selected stimulus can have an important role in how the body's immune system responds to disease. For example, IFN-α may inhibit hepatitis C, and MIP-1α and MIP-1β (also known as CCL3 and CCL4 respectively) may inhibit HIV-1 infection. Optimal balancing of the Th1/Th2 immune response presents the opportunity to use the immune system to treat and prevent a variety of diseases.

The Th1 immune response can be induced in mammals for example by introduction of bacterial or synthetic DNA containing unmethylated CpG dinucleotides, which immune response results from presentation of specific oligonucleotide sequences (e.g., unmethylated CpG) to receptors on certain immune cells known as pattern recognition receptors (PRRs). Certain of these PRRs are Toll-like receptors (TLRs).

TLRs are intimately involved in inducing the innate immune response in response to microbial infection. In vertebrates, TLRs consist of a family of at least eleven proteins (TLR1 to TLR11) that are known to recognize pathogen associated molecular patterns (PAMP). Some TLRs are located on the cell surface to detect and initiate a response to extracellular pathogens and other TLRs are located inside the cell to detect and initiate a response to intracellular pathogens. Table 1 provides a representation of TLRs, the known agonists therefore and the cell types known to contain the TLR (Diebold, S. S. et al. (2004) *Science* 303:1529-31; Liew, F. et al. (2005) *Nature* 5:446-58; Hemmi, H. et al. (2002) *Nat. Immunol.* 3:196-200; Jurk, M. et al., (2002) *Nat. Immunol.* 3:499; Lee, J. et al. (2003) *Proc. Natl. Acad. Sci. USA* 100:6646-51; Alexopoulou, L. (2001) *Nature* 413:732-38).

TABLE 1

| TLR Molecule | Known Agonist | Cell Types Containing Receptor |
|---|---|---|
| Cell Surface TLRs: | | |
| TLR2 | bacterial lipopeptides | Monocytes/macrophages<br>Myeloid dendritic cells<br>Mast cells |
| TLR4 | gram negative bacteria | Monocytes/macrophages<br>Myeloid dendritic cells<br>Mast cells<br>Intestinal epithelium |
| TLR5 | motile bacteria | Monocyte/macrophages<br>Dendritic cells<br>Intestinal epithelium |
| TLR6 | gram positive bacteria | Monocytes/macrophages<br>Mast cells<br>B lymphocytes |
| Endosomal TLRs: | | |
| TLR3 | double stranded viral or cellular RNA | Dendritic cells<br>B lymphocytes |
| TLR7 | single stranded viral or cellular RNA;<br>RNA-immunoglobulin complexes | Monocytes/macrophages<br>Plasmacytoid dendritic cells<br>B lymphocytes |
| TLR8 | single stranded viral or cellular RNA;<br>RNA-immunoglobulin complexes | Monocytes/macrophages<br>Dendritic cells<br>Mast cells |
| TLR9 | DNA containing unmethylated "CpG" or synthetic motifs;<br>DNA-immunoglobulin complexes | Monocytes/macrophages<br>Plasmacytoid dendritic cells<br>B lymphocytes |

The signal transduction pathway mediated by the interaction between a ligand and a TLR is shared among most members of the TLR family and involves a toll/IL-1 receptor (TIR domain), the myeloid differentiation marker 88 (MyD88), IL-1R-associated kinase (IRAK), interferon regulating factor (IRF), TNF-receptor-associated factor (TRAF), TGFβ-activated kinase1, IκB kinases, IκB, and NF-κB (see, for example: Akira, S. (2003) *J. Biol. Chem.* 278:38105 and Geller et al. (2008) *Curr. Drug Dev. Tech.* 5:29-38). More specifically, for TLRs 1, 2, 4, 5, 6, 7, 8, 9, and 11, this signaling cascade begins with a PAMP ligand interacting with and activating the membrane-bound TLR, which exists as a homo-dimer in the endosomal membrane or the cell surface. Following activation, the receptor undergoes a conformational change to allow recruitment of the TIR domain containing protein MyD88, which is an adapter protein that is common to all TLR signaling pathways except TLR3. MyD88 recruits IRAK4, which phosphorylates and activates IRAK1. The activated IRAK1 binds with TRAF6, which catalyzes the addition of polyubiquitin onto TRAF6. The addition of ubiquitin activates the TAK/TAB complex, which in turn phosphorylates IRFs, resulting in NF-κB release and transport to the nucleus. NF-κB in the nucleus induces the expression of proinflammatory genes (see, for example, Trinchieri and Sher (2007) *Nat. Rev. Immunol.* 7:179-90).

The selective localization of TLRs and the signaling generated therefrom, provides some insight into their role in the immune response. The immune response involves both an innate and an adaptive response based upon the subset of cells involved in the response. For example, the T helper cells involved in classical cell-mediated functions such as delayed-type hypersensitivity and activation of cytotoxic T lymphocytes (CTLs) are Th1 cells. This response is the body's innate response to antigen (e.g., viral infections, intracellular pathogens, and tumor cells), and results in a secretion of IFN-gamma and a concomitant activation of CTLs.

As a result of their involvement in regulating an inflammatory response, TLRs have been shown to play a role in the pathogenesis of many diseases, including autoimmunity, infectious disease, and inflammation (Papadimitraki et al. (2007) *J. Autoimmun.* 29:310-18; Sun et al. (2007) *Inflam. Allergy Drug Targets* 6:223-35; Diebold (2008) *Adv. Drug Deliv. Rev.* 60:813-23; Cook, D. N. et al. (2004) *Nature Immunol.* 5:975-79; Tse and Horner (2008) *Semin. Immunopathol.* 30:53-62; Tobias & Curtiss (2008) *Semin. Immunopathol.* 30:23-27; Ropert et al. (2008) *Semin. Immunopathol.* 30:41-51; Lee et al. (2008) *Semin. Immunopathol.* 30:3-9; Gao et al. (2008) *Semin. Immunopathol.* 30:29-40; Vijay-Kumar et al. (2008) *Semin. Immunopathol.* 30:11-21).

Studies have shown stimulation of an immune response using antisense oligonucleotides containing CpG dinucleotides (Zhao, Q. et al. (1996) *Biochem. Pharmacol.* 26:173-82). Subsequent studies showed that TLR9 recognizes unmethylated CpG motifs present in bacterial and synthetic DNA (Hemmi, H. et al. (2000) *Nature* 408:740-45). Other modifications of CpG-containing phosphorothioate oligonucleotides can also affect their ability to act through TLR9 and modulate the immune response (see, e.g., Zhao et al. (1996) *Biochem. Pharmacol.* 51:173-82; Zhao et al. (1996) *Biochem. Pharmacol.* 52:1537-44; Zhao et al. (1997) *Antisense Nucleic Acid Drug Dev.* 7:495-502; Zhao et al. (1999) *Bioorg. Med. Chem. Lett.* 9:3453-58; Zhao et al. (2000) *Bioorg. Med. Chem. Lett.* 10:1051-54; Yu et al. (2000) *Bioorg. Med. Chem. Lett.* 10:2585-88; Yu et al. (2001) *Bioorg. Med. Chem. Lett.* 11:2263-67; and Kandimalla et al. (2001) *Bioorg. Med. Chem.* 9:807-13). In addition, structure activity relationship studies have allowed identification of synthetic motifs and novel DNA-based structures that induce specific immune response profiles that are distinct from those resulting from unmethylated CpG dinucleotides. (Kandimalla, E. R. et al. (2005) *Proc. Natl. Acad. Sci. USA* 102:6925-30; Kandimalla, E. R. et al. (2003) *Proc. Natl. Acad. Sci. USA* 100:14303-08; Cong, Y. P. et al. (2003) *Biochem. Biophys. Res. Commun.* 310:1133-39; Kandimalla, E. R. et al. (2003) *Biochem. Biophys. Res. Commun.* 306:948-53; Kandimalla, E. R. et al. (2003) *Nucleic Acids Res.* 31:2393-400; Yu, D. et al. (2003) *Bioorg. Med. Chem.* 11:459-64; Bhagat, L. et al. (2003) *Biochem. Biophys. Res. Commun.* 300:853-61; Yu, D. et al. (2002) *Nucleic Acids Res.* 30:4460-69; Yu, D. et al. (2002) *J. Med. Chem.* 45:4540-48; Yu, D. et al. (2002) *Biochem. Biophys. Res. Commun.* 297:83-90; Kandimalla, E. R. et al. (2002) *Bioconjug. Chem.* 13:966-74; Yu, D. K. et al. (2002) *Nucleic Acids Res.* 30:1613-19; Yu, D. et al. (2001) *Bioorg. Med. Chem.* 9:2803-08; Yu, D. et al. (2001) *Bioorg. Med. Chem. Lett.* 11:2263-67; Kandimalla, E. R. et al. (2001) *Bioorg. Med. Chem.* 9:807-13; Yu, D. et al. (2000) *Bioorg. Med. Chem. Lett.* 10:2585-88; Putta, M. R. et al. (2006) *Nucleic Acids Res.* 34:3231-38). However, until recently, natural ligands for TLR7 and TLR8 were unknown.

It has been shown that TLR7 and TLR8 recognize viral and synthetic single-stranded RNAs and small molecules, including a number of nucleosides (Diebold, S. S., et al. (2004) *Science* 303:1529-31). Diebold et al. show that the IFN-α response to influenza virus requires endosomal recognition of influenza genomic RNA and signaling by means of TLR7 and MyD88 and identify ssRNA as a ligand for TLR7. Certain synthetic compounds, the imidazoquinolones, imiquimod (R-837), and resiquimod (R-848) are ligands of TLR7 and TLR8 (Hemmi, H. et al. (2002) *Nat. Immunol* 3:196-200; Jurk, M. et al. (2002) *Nat. Immunol* 3:499). In addition, certain guanosine analogs, such as 7-deaza-G, 7-thia-8-oxo-G (TOG), and 7-allyl-8-oxo-G (loxoribine), have been shown to activate TLR7 at high concentrations (Lee, J. et al. (2003) *Proc. Natl. Acad. Sci. USA* 100:6646-51). However, these small molecules, e.g., imiquimod, are also known to act through other receptors (Schon, M. P. et al. (2006) *J. Invest. Dermatol.* 126:1338-47).

The lack of any known specific ssRNA motif for TLR7 or TLR8 recognition and the potentially wide range of stimulatory ssRNA molecules suggest that TLR7 and TLR8 can recognize both self and viral RNA. Recently it was shown that certain GU-rich oligoribonucleotides are immunostimulatory and act through TLR7 and TLR8 (Heil et al. (2004) *Science* 303:1526-29; Lipford et al., International Publication No. WO 03/086280; Wagner et al., International Publication No. WO 98/32462) when complexed with N-[1-(2,3-Dioleoyloxy)propyl]-N,N,N trimethylammoniummethylsulfate (DOTAP) or other lipid agents. However, RNA molecules have been used for many years, for example as ribozymes and, more recently, siRNA and microRNA, and RNA employed as ribozymes, siRNA, and microRNA contain GU dinucleotides. In addition, a number of these RNA molecules have been shown to elicit immune responses through TLR stimulation in the presence of lipids (Kariko et al. (2005) *Immunity* 23:165-75; Ma, Z. et al. (2005) *Biochem. Biophys. Res. Commun.* 330:755-59). However, the instability of these RNA molecules has hindered progress in using and applying these molecules in many areas (e.g., prevention and treatment of human disease).

Oligonucleotides and oligodeoxynucleotides containing a ribose or deoxyribose sugar have been used in a wide variety of fields, including but not limited to diagnostic probing, PCR priming, antisense inhibition of gene expression, siRNA, microRNA, aptamers, ribozymes, and immunotherapeutic agents based on Toll-like Receptors (TLRs). More recently, many publications have demonstrated the use of oligodeoxynucleotides as immune modulatory agents and their use alone or as adjuvants in immunotherapy applications for many diseases, such as allergy, asthma, autoimmunity, cancer, and infectious diseases.

The fact that DNA oligonucleotides are recognized by TLR9, while RNA oligonucleotides are recognized by TLR7 and/or TLR8 is most likely due to differences in the structural conformations between DNA and RNA. However, the chemical differences between DNA and RNA also make DNA far more chemically and enzymatically stable than RNA.

RNA is rapidly degraded by ubiquitous extracellular ribonucleases (RNases), which ensure that little, if any, self-ssRNA reaches the antigen-presenting cells. Exonuclease degradation of nucleic acids is predominantly of 3'-nuclease digestion with a smaller percentage through 5'-exonuclease action. In addition to exonuclease digestion, RNA can also be degraded by endonuclease activity of RNAses. RNA-based molecules have so far had to be complexed with lipids to provide stability against nucleases.

While providing an essential function of preventing autoimmune reactivity, these ribonucleases also present a substantial problem for any synthetic ssRNA molecule designed to be exploited for immunotherapy, as ribonucleases will rapidly degrade both synthetic and natural ssRNA. To overcome this hurdle, protection of ssRNA molecules from degradation has been attempted by encapsulating the ssRNA in liposomes, condensing it with polyethylenimine, or complexing it to molecules such as N-[1-(2,3 dioleoyloxy)-propyl]-N,N,N-trimethylammonium methyl-sulfate (DOTAP). However, these protective measures are secondary measures applied to a still unstable ssRNA, and the effects of these protective measures on the in vivo efficacy and immune modulatory activity of ssRNA (natural or synthetic) remain unclear.

Agrawal et al. (U.S. Patent Application Publication No. 2008/0171712) describe a novel class of SIMRA compositions which bind to TLR7 and TLR8. However, a challenge remains to develop compounds that selectively bind to TLR7. Ideally, this challenge might be met through the design of inherently stable RNA-based molecules that can act as new immunotherapic agents, which will find use in a number of clinically relevant applications, such as improving the effects of vaccination when co-administered or treating and/or preventing diseases when invoking or enhancing an immune response is beneficial, for example cancer, autoimmune disorders, airway inflammation, inflammatory disorders, infectious diseases, skin disorders, allergy, asthma, or diseases caused by pathogens.

BRIEF SUMMARY OF THE INVENTION

In a first aspect, the invention provides stabilized immune modulatory RNA (SIMRA) compounds, further defined below, that specifically activate TLR7 and their use for inducing and/or enhancing an immune response through TLR7. The chemical entities according to the invention provide immune response inducing and/or enhancing compounds that are substantially more effective at inducing an immune response and substantially less susceptible to degradation. The methods according to the invention enable using the TLR7 specific SIMRAs to modify the cytokine and/or chemokine profile for immunotherapy applications.

In another embodiment of the first aspect, the invention provides a TLR7-specific SIMRA compound as an adjuvant.

In a second aspect, the invention provides pharmaceutical compositions. These compositions comprise at least one of the TLR7-specific SIMRA compositions of the invention and a physiologically acceptable or pharmaceutically acceptable carrier.

In a third aspect, the invention provides a method for generating an immune response in an individual, the method comprising administering to the vertebrate at least one of the TLR7-specific SIMRA compounds according to the invention.

In a fourth aspect, the invention provides a method for therapeutically treating an individual having a disease or disorder where inducing and/or enhancing an immune response would be beneficial, for example cancer, autoimmune disorders, airway inflammation, inflammatory disorders, infectious diseases, skin disorders, allergy, asthma, or diseases caused by pathogens, such method comprising administering to the patient having such a disorder or disease at least one of the TLR7-specific SIMRA compounds according to the invention in a pharmaceutically effective amount.

In a fifth aspect, the invention provides a method for preventing a disease or disorder in a vertebrate where inducing and/or enhancing an immune response would be beneficial, for example cancer, an autoimmune disorder, airway inflammation, inflammatory disorders, infectious disease, skin disorders, allergy, asthma, or diseases caused by a pathogen, such method comprising administering to a vertebrate that is susceptible to such a disorder or disease at least one of the TLR7-specific SIMRA compounds according to the invention in a pharmaceutically effective amount.

In a sixth aspect, the invention provides a method of isolating cells capable of producing cytokine or chemokines (e.g., immune cells, PBMCs), culturing such cells under standard cell culture conditions, ex vivo treating such cells with at least one of the TLR7-specific SIMRA compounds of the invention such that the isolated cells produce or secrete increased levels of cytokines or chemokines, and administering or re-administering the treated cells to a patient in need of cytokine or chemokine therapy for the prevention or treatment of disease.

In a further embodiment of this aspect of the invention, the patient in need of cytokine or chemokine therapy for prevention or treatment of disease is administered the isolated, TLR7-specific SIMRA-treated cells of the sixth aspect, in combination with one or more TLR7-specific SIMRA compounds of the invention and/or one or more TLR7 and/or TLR8 agonist.

BRIEF DESCRIPTION OF THE DRAWINGS

FIG. 1 is a synthetic scheme for the parallel synthesis of TLR7-specific SIMRA compounds of the invention. DMTr=4,4'-dimethoxytrityl; CE=cyanoethyl. TLR7-specific SIMRA compounds of the invention were synthesized according to Example 1.

DETAILED DESCRIPTION OF THE PREFERRED EMBODIMENTS

The invention relates to the therapeutic use of oligoribonucleotides as immune modulatory agents for immunotherapy applications. Specifically, the invention provides RNA-based oligonucleotides with improved in vivo stability that selectively modulate the immune response through TLR7 (TLR7-specific SIMRA compounds). By initiating diverse innate and acquired immune response mechanisms, for example through activation of dendritic cells and other antigen-presenting cells with stable TLR7-specific SIMRA compounds, the resulting cytokine profile can lead to the destruction of pathogens, infected cells, or tumor cells and development of antigen-specific antibody and CTL responses. Thus, the invention provides a set of TLR7-specific SIMRA compounds, each having its own unique immune regulatory characteristics. In this way, the scope and nature of the immune response can be customized for distinct medical indications by providing the TLR7-specific SIMRA compound having the desired set of immune modulatory characteristics for that indication. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for using TLR7-specific SIMRA compounds to enhance the immune response. Such methods will find use in immunotherapy applications such as, but not limited to, treatment of cancer, autoimmune disorders, asthma, respiratory allergies, food allergies, skin allergies, and bacteria, parasitic, and viral infections and as vaccine adjuvants in adult and pediatric human and veterinary applications. Thus, the invention further provides TLR7-specific SIMRA compounds having optimal levels of immune modulatory effect for immunotherapy and methods for making and using such compounds. In addition, TLR7-specific SIMRA compounds of the invention are useful as adjuvants or in combination with an agent useful for treating the disease or condition that does not abolish the immune modulatory effect of the TLR7-specific SIMRA compound for prevention and treatment of diseases.

DEFINITIONS

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Arabinonucleosides of the invention include, but are not limited to, arabino-G, arabino-C, arabino-U, arabino-A. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides, and 2'-O-methoxyethoxyribonucleosides or 2'-β-methoxyethoxyarabinosides.

The term "3'", when used directionally, generally refers to a region or position in a polynucleotide or oligonucleotide 3' (toward the 3' position of the sugar) from another region or position in the same polynucleotide or oligonucleotide.

The term "5'", when used directionally, generally refers to a region or position in a polynucleotide or oligonucleotide 5' (toward the 5' position of the sugar) from another region or position in the same polynucleotide or oligonucleotide.

The term "about" generally means that the exact number is not critical. Thus, the number of ribonucleoside residues in the oligoribonucleotides is not critical, and oligoribonucleotides having one or two fewer ribonucleoside or arabinonucleoside residues, or from one to several additional ribonucleoside or arabinonucleoside residues are contemplated as equivalents of each of the embodiments described above.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, inflammation in the respiratory tract caused by infectious allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies, and skin allergies.

The term "antigen" generally refers to a substance that is recognized and selectively bound by an antibody or by a T cell antigen receptor. Antigens may include but are not limited to peptides, proteins, nucleosides, nucleotides, and combinations thereof. Antigens may be natural or synthetic and generally induce an immune response that is specific for that antigen.

The term "autoimmune disorder" generally refers to disorders in which "self" antigen undergo attack by the immune system.

Blocking 3' or 5' degradation or "cap" or "capping" means that the 3' or 5' end of the oligoribonucleotide is attached to another molecule (e.g., linker or other non-RNA nucleotide) to sufficiently inhibit nuclease degradation (e.g., 3' exonuclease degradation).

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences*, 18th Edition, ed. A. Gennaro, Mack Publishing Co., Easton, Pa., 1990.

The term "co-administration" generally refers to the administration of at least two different substances sufficiently close in time to modulate an immune response. Co-administration includes simultaneous administration of at least two different substances.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term "immune modulatory oligoribonucleotide" generally refers to an oligoribonucleotide that induces or represses an immune response when administered to a vertebrate, such as a fish, fowl, or mammal.

The term "in combination with" generally means in the course of treating the same disease in the same patient, and includes administering a TLR7-specific SIMRA compound and an agent useful for treating the disease or condition that does not abolish the immune modulatory effect of the TLR7-specific SIMRA compound. Such administration can be in any order, including simultaneous administration or co-administration, as well as temporally spaced order from a few seconds up to several days apart, or from a few minutes to a few days apart, or from a few minutes to a few hours apart. Such combination treatment may also include more than a single administration of a TLR7-specific SIMRA compound, and/or independently the agent. The administration of the TLR7-specific SIMRA compound and the agent may be by the same or different routes.

The term "individual" or "subject" generally refers to a mammal, such as a human. Mammals generally include, but are not limited to, humans, non-human primates, rats, mice, cats, dogs, horses, cattle, cows, pigs, sheep, and rabbits.

The term "linear synthesis" generally refers to a synthesis that starts at one end of the immune modulatory oligoribonucleotide and progresses linearly to the other end. Linear synthesis permits incorporation of either identical or non-identical (in terms of length, base composition and/or chemical modifications incorporated) monomeric units into the immune modulatory oligoribonucleotides.

The term "linker" generally refers to any moiety that can be attached to an oligoribonucleotide by way of covalent or non-covalent bonding through a sugar, a base, or the backbone. The linker can be used to attach two or more nucleosides or can be attached to the 5' and/or 3' terminal nucleotide in the oligoribonucleotide. Such linker can be either a non-nucleotidic linker or a nucleotidic linker.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, or uracil. In some embodiments, the modified nucleoside is a 2'-substituted ribonucleoside, an arabinonucleoside, or a 2'-deoxy-2'-substituted-arabinoside that can be substituted into selected positions of the oligoribonucleotide to improve stability without interfering with TLR7 activity.

The term "modulation" or "stimulation" generally refers to change, such as an increase in a response or qualitative difference in a response, which can arise from eliciting and/or enhancement of a response.

The term "non-nucleotidic linker" generally refers to a chemical moiety other than a nucleotidic linkage that can be attached to an oligoribonucleotide by way of covalent or non-covalent bonding. Preferably such non-nucleotidic linker is from about 2 angstroms to about 200 angstroms in length, and may be either in a cis or trans orientation.

The term "nucleotidic linkage" generally refers to a chemical linkage to join two nucleosides through their sugars (e.g., 3'-3',2'-3',2'-5',3'-5') consisting of a phosphate, non-phosphate, charged, or neutral group (e.g., phosphodiester, phosphorothioate or phosphorodithioate) between adjacent nucleosides.

The term "peptide" generally refers to polypeptides that are of sufficient length and composition to affect a biological response, e.g., antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization, and methylation.

The terms "pharmaceutically acceptable" or "physiologically acceptable" generally refer to a material that does not interfere with the effectiveness of a compound according to the invention and that is compatible with a biological system such as a cell, cell culture, tissue, or organism. Preferably, the biological system is a living organism, such as a vertebrate.

The term "pharmaceutically effective amount" generally refers to an amount sufficient to affect a desired biological effect, such as a beneficial result. Thus, a "pharmaceutically effective amount" will depend upon the context in which it is being administered. A pharmaceutically effective amount may be administered in one or more prophylactic or therapeutic administrations.

The term "SIMRA" generally refers to stabilized immune modulatory RNA compounds, wherein the compounds may contain single-stranded RNA (ssRNA) and/or double-stranded RNA (dsRNA), and modifications to protect or stabilize its 3' ends (e.g., by blocking 3' degradation or by capping the 3' ends or by linking the 3' ends of two or more oligoribonucleotides), provided that the SIMRA is or would be more stable in vivo than an unmodified oligoribonucleotide and, thus, affect its immune modulatory capabilities. The SIMRA may contain modified oligoribonucleotides. The SIMRA compound may also contain modifications to protect its 5' ends (e.g., by blocking 5' degradation or capping the 5' ends) to further improve the stability of the oligoribonucleotide(s). The SIMRA can be linear or branched, with nucleic acids being polymers of ribonucleosides linked through, for example, phosphodiester, phosphorothioate, or alternate linkages. A SIMRA may consist of a purine (adenine (A) or guanine (G) or derivatives thereof (e.g., 7-deaza-G, arabino-G and arabino-A)) or pyrimidine (cytosine (C) or uracil (U), or derivatives thereof (e.g., arabino-C and arabino-U)) base covalently attached to a ribose sugar residue or a derivative thereof.

The term "treatment" generally refers to an approach intended to obtain a beneficial or desired result, which may include alleviation of symptoms, or delaying or ameliorating a disease progression.

The term "viral disease" generally refers to a disease that has a virus as its etiologic agent, including but not limited to hepatitis B, hepatitis C, influenza, acquired immunodeficiency syndrome (AIDS), and herpes zoster.

In a first aspect, the invention provides TLR7-specific SIMRA compounds. The instant application shows that modification of an immune modulatory oligoribonucleotide to protect its 3' end (e.g., by blocking 3' degradation or capping the 3' end or by linking the 3' ends of two or more oligoribonucleotides) surprisingly affects its immune modulatory capabilities. In addition, it has been determined that this protection surprisingly improves the stability of the oligoribonucleotides, removing the need for lipid association or other means of protection. Further, blocking 5' degradation or capping the 5' end in addition to or in combination with protecting the 3'-end can also improve the stability of the oligoribonucleotide.

In the present invention, activation of TLR7 and induction of unique immune responses (e.g., changes in cytokine and/or chemokine profiles) with SIMRA compounds is demonstrated. Thus, the instant application surprisingly shows that through activation of TLR7 cytokine and/or chemokine, profiles associated therewith can be modulated by using modified chemical structures, including modified bases, modified sugars, backbone, linkers, linkages, and/or caps as part of an immune modulatory oligoribonucleotide.

In one embodiment, the invention provides an immune modulatory compound comprising at least two RNA-based oligonucleotides linked at their 3' ends, or an internucleoside linkage or a functionalized nucleobase or sugar to a non-nucleotidic linker. Such embodiment of the invention may have at least one accessible 5' end, which may be capped or uncapped. It has been determined that this structure provides further stability (e.g., inhibition of exonuclease activity) to the TLR7-specific SIMRA compounds without the need for lipid association or other protection. An "accessible 5' end" means that the 5'-terminus of the TLR7-specific SIMRA is not modified in such a way as to prevent the TLR7-specific SIMRA compound from modulating an immune response through TLR7.

In another embodiment of this aspect of the invention comprises at least two oligoribonucleotides, wherein the immune modulatory compound has a structure including, but not limited to, Formulas I-IV in Table 2.

TABLE 2

Oligoribonucleotide Formulas I-IV

Formula I

5' Domain A 3'—X—3' Domain B 5'

Formula II

5' Domain A 3'
         \\   /
          3' 5'
           X
           3'
        Domain C
           |
           5'

Formula III

5'—Domain A—X—Domain B—3'
3'—Domain B—X—Domain A—5'

Formula IV

[5'—Domain A—X—Domain B—3' 5'—Domain A—X—Domain B—3']$_n$
 3'—Domain B—X—Domain A—5'

Domains A, B, and C may be independently from about 2 to about 35 ribonucleotides, and in some embodiments from about 2 to about 20, or from about 2 to about 12, or from about 2 to about 11, or from about 2 to about 8 ribonucleotides in length. Domains A, B, and C may or may not be identical. Domains A, B, and C may independently be 5'-3' or 2'-5' RNA having or not having a self-complementary domain, a homo or hetero ribonucleotide sequence, or a linker. As used in Formula IV, "n" may be from 1 to an unlimited number.

"X" is a linker joining or capping Domains A, B, and/or C that may be through a 3' or 5' linkage, a phosphate group, a nucleobase, a non-RNA nucleotide, or a non-nucleotidic linker that may be aliphatic, aromatic, aryl, cyclic, chiral, achiral, a peptide, a carbohydrate, a lipid, a fatty acid, mono- tri- or hexapolyethylene glycol, or a heterocyclic moiety, or combinations thereof.

In a further embodiment, the invention provides a TLR7-specific SIMRA compound comprising at least two oligoribonucleotides linked by a non-nucleotidic linker, wherein the sequences of the immune modulatory oligoribonucleotides may be at least partially self-complementary. The complementary sequence of the oligoribonucleotides allows for intermolecular hydrogen bonding thereby giving the oligoribonucleotides secondary structure. Additional oligoribonucleotides can bind together thereby creating a chain, or multimers, of oligoribonucleotides according to the invention as for example in Formula IV.

Similar considerations apply to intermolecular base pairing between immune modulatory oligoribonucleotides of different base sequence. Thus, where a plurality of immune modulatory oligoribonucleotides is used together, the plurality of immune modulatory oligoribonucleotides may, but need not, include sequences that are at least partially complementary to one another. In one embodiment the plurality of immune modulatory oligoribonucleotides includes an immune modulatory oligoribonucleotide having a first sequence and an immune modulatory oligoribonucleotide having a second sequence, wherein the first sequence and the second sequence are at least 40 percent or at least 50 percent complementary. For example, as between two 8-mers that are at least 50 percent complementary, they may form 4, 5, 6, 7, or 8 G-C, A-U, and/or G-U wobble basepairs. Such basepairs may, but need not necessarily, involve bases located at either end of the complementary immune modulatory oligoribonucleotides. The degree of complementarity may depend on the alignment between immune modulatory oligoribonucleotides, and such alignment may or may not include single- or multiple-nucleoside overhangs. In other embodiments, the degree of complementarity is at least 60 percent, at least 70 percent, at least 80 percent, at least 90 percent or 100 percent.

As would be recognized by one skilled in the art, the depicted immune modulatory compounds may have secondary structure because the sequences of the domains are complementary allowing for intermolecular hydrogen bonding. Moreover, as indicated by Formulas III and IV in Table 2, additional linked RNA-based oligonucleotides can bind through intermolecular hydrogen bonding thereby creating a chain, or multimers, wherein any number of linked RNA-based oligonucleotides may be incorporated.

In another embodiment, the invention provides an immune modulatory compound comprising at least two RNA-based oligonucleotides linked at their 3' or 5' ends, or through an internucleoside linkage or a functionalized nucleobase or sugar to a non-nucleotidic linker, and wherein a linker (e.g., cap) is attached to at least one 5' end. It has been determined that this structure provides further stability (e.g., inhibition of exonuclease activity) to the TLR7-specific SIMRA compounds. The 5'-terminus of the TLR7-specific SIMRA is not modified in such a way as to prevent the TLR7-specific SIMRA compound from modulating an immune response through TLR7.

In some embodiments, the oligoribonucleotides each independently have from about 2 to about 35 ribonucleoside residues. Thus in certain embodiments the oligoribonucleotide can independently be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 ribonucleotides long. Preferably the oligoribonucleotide is from about 4 to about 30 ribonucleoside residues, more preferably from about 4 to about 20 ribonucleoside residues or from about 4 to about 11 ribonucleoside residues. In some embodiments, the immune modulatory oligoribonucleotides comprise oligoribonucleotides having from about 1 to about 18, or from about 1 to about 11, or from about 5 to about 14 ribonucleoside residues. In some embodiments, one or more of the oligoribonucleotides have 11 ribonucleotides or from about 8 to about 14 ribonucleotides or from about 10 to about 12 ribonucleotides. In the context of immune modulatory oligoribonucleotides, preferred embodiments have from about 1 to about 35 ribonucleotides, preferably from about 5 to about 26 ribonucleotides, more preferably from about 13 to about 26 ribonucleotides. Preferably, the immune modulatory oligoribonucleotide comprises at least one phosphodiester, phosphorothioate or phosphorodithioate interribonucleoside linkage.

In exemplary embodiments each ribonucleoside unit includes a heterocyclic base and a pentofuranosyl, trehalose, arabinose, 2'-deoxy-2'-substituted arabinose, 2'-O-substituted ribose or arabinose or hexose sugar group. The ribonucleoside residues can be coupled to each other by any of the numerous known interribonucleoside linkages. Such interribonucleoside linkages include, without limitation, phosphodiester (Po), phosphorothioate (Ps), phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone interribonucleoside linkages, or any combination thereof.

Additionally, exemplary oligoribonucleotide may be coupled with any combination of such interribonucleoside linkages, including, without limitation alternating phosphodiester and phosphorothioate linkages (e.g., $N_{1Po}N_{2Ps}N_{3Po}N_{nPs}$, where N is a ribonucleoside according to the invention), segments of phosphodiester linkages followed by segments of phosphorothioate linkages (e.g., $N_{1Po}N_{2Po}N_{3Po}N_{nPo}N_{1Ps}N_{2Ps}N_{3Ps}N_{nPs}$, where N is a ribonucleoside according to the invention), and segments of phosphorothioate linkages followed by segments of phosphodiester linkages (e.g., $N_{1Ps}N_{2Ps}N_{3Ps}N_{nPs}N_{1Po}N_{2Po}N_{3Po}N_{nPo}$, where N is a ribonucleoside according to the invention).

Possible sites of conjugation for the ribonucleotide are indicated in Formula V, below, wherein B represents a heterocyclic base.

Formula V

The TLR7-specific SIMRA compounds of the invention can include naturally occurring ribonucleosides, modified ribonucleosides, or mixtures thereof.

In the present invention, TLR7-specific SIMRA compounds are recognized by human TLR7 by incorporation of certain chemical modification(s) resulting in an induction of immune responses. Such chemical modifications include, but are not limited to, guanine analogues such as 7-deaza-G, ara-G, 6-thio-G, Inosine, Iso-G, loxoribine, TOG (7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, and 1-(B-D-ribofuranosyl)-2-oxo-7-deaza-8-methyl-purine. Chemical modifications also include, but are not limited to, adenine analogues such as 9-benzyl-8-hydroxy-2-(2-methoxyethoxy)adenine, 2-Amino-N2-O—, methyladenosine, 8-Aza-7-deaza-A, 7-deaza-A, ara-A, Vidarabine, 2-Aminoadenosine, N1-Methyladenosine, 8-Azaadenosine, and 5-Iodotubercidin. Chemical modifications also include, but are not limited to, cytosine and uracil analogues such as pseudouridine, ara-C, ara-U, 5-methylcytidine, 4-thiouridine, N4-ethyluridine, zebularine, 5-aminoallyluridine, N3-methyluridine, and 5-fluorouridine.

The "immune modulatory oligoribonucleotides" according to the invention are TLR7-specific SIMRA compounds that comprise at least two oligoribonucleotides linked covalently or non-covalently at their 3'- or 2'-ends or functionalized ribose or functionalized ribonucleobase via a non-nucleotidic or a nucleotidic linker. Non-covalent linkages include, but are not limited to, electrostatic interaction, hydrophobic interactions, π-stacking interactions, and hydrogen bonding.

In some embodiments, the non-nucleotidic linkers may include, but are not limited to, those listed in Table 3.

TABLE 3

Representative Non-nucleotidic Linkers

Glycerol (1,2,3-Propanetriol)

1,2,4-Butanetriol 2-(hydroxymethyl)-1,3-propanediol 2-(hydroxymethyl)1,4-butanediol 1,3,5-Pentanetriol

TABLE 3-continued

Representative Non-nucleotidic Linkers

HO-C(CH₂OH)₂-OH structure
1,1,1-Tris(hydroxymethyl)ethane

HO-CH₂-CH₂-OH
Ethylene glycol

HO-(CH₂)₃-OH
1,3-Propanediol

HO-(CH₂)₄-OH
1,4-Butanediol

HO-(CH₂)₅-OH
1,5-Pentanediol

HO-(CH₂)₆-OH
1,6-Hexanediol

HO-(CH₂)₇-OH
1,7-Heptanediol

HO-(CH₂)₈-OH
1,8-Octanediol

HO-(CH₂)₉-OH
1,9-Nonanediol

HO-(CH₂)₁₂-OH
1,12-Dodecanediol

In some embodiments, the small molecule linker is glycerol or a glycerol homolog of the formula HO—(CH$_2$)$_o$—CH(OH)—(CH$_2$)$_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH$_2$)$_m$—C(O)NH—CH$_2$—CH(OH)—CH$_2$—NHC(O)—(CH$_2$)$_m$—OH, wherein m is an integer from 0 to about 10, from 0 to about 6, from 2 to about 6, or from 2 to about 4.

Some non-nucleotidic linkers according to the invention permit attachment of more than two oligoribonucleotides, as depicted by Formula II in Table 2. For example, the small molecule linker glycerol has three hydroxyl groups to which oligoribonucleotides may be covalently attached. Some immune modulatory oligoribonucleotides according to the invention, therefore, comprise more than two oligoribonucleotides (e.g., a Domain C and so on, the additional domains comprise oligoribonucleotides as defined above for Domains A, B, C, and D) linked at their 3' ends to a non-nucleotidic linker.

The immune modulatory oligoribonucleotides of the invention may conveniently be synthesized using an automated synthesizer and phosphoramidite approach. In some embodiments, the immune modulatory oligoribonucleotides are synthesized by a linear synthesis approach. An alternative mode of synthesis is "parallel synthesis," in which synthesis proceeds outward from a central linker moiety (see FIG. 1). A solid support attached linker can be used for parallel synthesis, as is described in U.S. Pat. No. 5,912,332. Alternatively, a universal solid support (such as phosphate attached controlled pore glass) support can be used.

Parallel synthesis of immune modulatory oligoribonucleotides has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immune modulatory oligoribonucleotide product.

At the end of the synthesis protocol, the immune modulatory oligoribonucleotides may conveniently be deprotected with concentrated ammonia solution or as recommended by the phosphoramidite supplier, if a modified nucleoside is incorporated. The product immune modulatory oligoribonucleotide is preferably purified by reversed phase HPLC, detritylated, desalted and dialyzed.

Table 4 shows TLR7-specific SIMRA compounds according to the invention. Unless otherwise specified, all nucleosides are ribonucleosides and all linkages are phosphorothioate.

TABLE 4

Stabilized RNA-based Immune Modulatory Oligonucleotide (SIMRA) Sequences

| SIMRA# | SEQ ID NO: | Sequences and Modification | SIMRA Structure |
|---|---|---|---|
| 1 | 1 | 5'-UUG$_1$CUG$_1$AG$_1$CUU-X-UUCG$_1$AG$_1$UCG$_1$UU-5' | 5'-SEQ ID NO: 1-3'-X-3'-SEQ ID NO: 1-5' |
| 2 | 2 | 5'-UG$_1$AUG$_1$ACG$_1$AUU-X-UUAG$_1$CAG$_1$UAG$_1$U-5' | 5'-SEQ ID NO: 2-3'-X-3'-SEQ ID NO: 2-5' |
| 3 | 3 | 5'-UG$_1$ACG$_1$AUG$_1$AUU-X-UUAG$_1$UAG$_1$CAG$_1$U-5' | 5'-SEQ ID NO: 3-3'-X-3'-SEQ ID NO: 3-5' |
| 4 | 4 | 5'-CUUG$_1$UG$_1$AG$_1$CUU-X-UUCG$_1$AG$_1$UG$_1$UUC-5' | 5'-SEQ ID NO: 4-3'-X-3'-SEQ ID NO: 4-5' |
| 5 | 5 | 5'-CUG$_1$AG$_1$AAG$_1$CUU-X-UUCG$_1$AAG$_1$AG$_1$UC-5' | 5'-SEQ ID NO: 5-3'-X-3'-SEQ ID NO: 5-5' |
| 6 | 6 | 5'-CUG$_1$ACG$_1$AG$_1$CUU-X-UUCG$_1$AG$_1$CAG$_1$UC-5' | 5'-SEQ ID NO: 6-3'-X-3'-SEQ ID NO: 6-5' |
| 7 | 7 | 5'-ACUUG$_1$ACUUG$_1$A-X-AG$_1$UUCAG$_1$UUCA-5' | 5'-SEQ ID NO: 7-3'-X-3'-SEQ ID NO: 7-5' |

TABLE 4-continued

Stabilized RNA-based Immune Modulatory Oligonucleotide (SIMRA) Sequences

| SIMRA# | SEQ ID NO: | Sequences and Modification | SIMRA Structure |
|---|---|---|---|
| 8 | 8 | 5'-ACUUG$_1$ACG$_1$AUU-X-UUAG$_1$CAG$_1$UUCA-5' | 5'-SEQ ID NO: 8-3'-X-3'-SEQ ID NO: 8-5' |
| 9 | 9 | 5'-ACUUG$_1$ACCUUU-X-UUUCCAG$_1$UUCA-5' | 5'-SEQ ID NO: 9-3'-X-3'-SEQ ID NO: 9-5' |
| 10 | 10 | 5'-ACUUG$_1$ACCUG$_1$U-X-UG$_1$UCCAG$_1$UUCA-5' | 5'-SEQ ID NO: 10-3'-X-3'-SEQ ID NO: 10-5' |
| 11 | 11 | 5'-ACUUG$_1$AAG$_1$CUU-X-UUCG$_1$AAG$_1$UUCA-5' | 5'-SEQ ID NO: 11-3'-X-3'-SEQ ID NO: 11-5' |
| 12 | 12 | 5'-ACUUG$_1$AACUUG$_1$-X-G$_1$UUCAAG$_1$UUCA-5' | 5'-SEQ ID NO: 12-3'-X-3'-SEQ ID NO: 12-5' |
| 13 | 13 | 5'-ACUUG$_1$AAACCU-X-UCCAAAG$_1$UUCA-5' | 5'-SEQ ID NO: 13-3'-X-3'-SEQ ID NO: 13-5' |
| 14 | 14 | 5'-ACUG$_1$CG$_1$AG$_1$CUU-X-UUCG$_1$AG$_1$CG$_1$UCA-5' | 5'-SEQ ID NO: 14-3'-X-3'-SEQ ID NO: 14-5' |
| 15 | 15 | 5'-ACUG$_1$AG$_1$AG$_1$CUU-X-UUCG$_1$AG$_1$AG$_1$UCA-5' | 5'-SEQ ID NO: 15-3'-X-3'-SEQ ID NO: 15-5' |
| 16 | 16 | 5'-ACG$_1$UG$_1$AAG$_1$CUU-X-UUCG$_1$AAG$_1$UG$_1$CA-5' | 5'-SEQ ID NO: 16-3'-X-3'-SEQ ID NO: 16-5' |
| 17 | 17 | 5'-ACG$_1$CUG$_1$AG$_1$CUU-X-UUCG$_1$AG$_1$UCG$_1$CA-5' | 5'-SEQ ID NO: 17-3'-X-3'-SEQ ID NO: 17-5' |
| 18 | 18 | 5'-AAUUG$_1$ACG$_1$CUU-X-UUCG$_1$CAG$_1$UUAA-5' | 5'-SEQ ID NO: 18-3'-X-3'-SEQ ID NO: 18-5' |
| 19 | 19 | 5'-AAUUG$_1$ACG$_1$CUG$_1$-X-G$_1$UCG$_1$CAG$_1$UUAA-5' | 5'-SEQ ID NO: 19-3'-X-3'-SEQ ID NO: 19-5' |
| 20 | 20 | 5'-AAG$_1$UG$_1$CG$_1$ACUU-X-UUCAG$_1$CG$_1$UG$_1$AA-5' | 5'-SEQ ID NO: 20-3'-X-3'-SEQ ID NO: 20-5' |
| 21 | 21 | 5'-AAG$_1$UG$_1$ACG$_1$CUU-X-UUCG$_1$CAG$_1$UG$_1$AA-5' | 5'-SEQ ID NO: 21-3'-X-3'-SEQ ID NO: 21-5' |
| 22 | 22 | 5'-AAG$_1$UG$_1$ACG$_1$AUU-X-UUAG$_1$CAG$_1$UG$_1$AA-5' | 5'-SEQ ID NO: 22-3'-X-3'-SEQ ID NO: 22-5' |
| 23 | 23 | 5'-AACUUG$_1$AG$_1$CUU-X-UUCG$_1$AG$_1$UUCAA-5' | 5'-SEQ ID NO: 23-3'-X-3'-SEQ ID NO: 23-5' |
| 24 | 24 | 5'-AACUG$_1$CG$_1$ACUU-X-UUCAG$_1$CG$_1$UCAA-5' | 5'-SEQ ID NO: 24-3'-X-3'-SEQ ID NO: 24-5' |
| 25 | 25 | 5'-AACUG$_1$ACG$_1$CUU-X-UUCG$_1$CAG$_1$UCAA-5' | 5'-SEQ ID NO: 25-3'-X-3'-SEQ ID NO: 25-5' |
| 26 | 26 | 5'-AACUG$_1$ACG$_1$CUG$_1$-X-G$_1$UCG$_1$CAG$_1$UCAA-5' | 5'-SEQ ID NO: 26-3'-X-3'-SEQ ID NO: 26-5' |
| 27 | 27 | 5'-UG$_1$AUG$_1$AAG$_1$CUU-X-UUCG$_1$AAG$_1$UAG$_1$U-5' | 5'-SEQ ID NO: 27-3'-X-3'-SEQ ID NO: 27-5' |
| 28 | 28 | 5'-AACUG$_1$AAG$_1$CUU-X-UUCG$_1$AAG$_1$UCAA-5' | 5'-SEQ ID NO: 28-3'-X-3'-SEQ ID NO: 28-5' |
| 29 | 29 | 5'-AACUG$_1$AAG$_1$CUG$_1$-X-G$_1$UCG$_1$AAG$_1$UCAA-5' | 5'-SEQ ID NO: 29-3'-X-3'-SEQ ID NO: 29-5' |
| 30 | 30 | 5'-AAUUG$_1$AAG$_1$CUU-X-UUCG$_1$AAG$_1$UUAA-5' | 5'-SEQ ID NO: 30-3'-X-3'-SEQ ID NO: 30-5' |
| 31 | 31 | 5'-AAUUG$_1$AAG$_1$CUG$_1$-X-G$_1$UCG$_1$AAG$_1$UUAA-5' | 5'-SEQ ID NO: 31-3'-X-3'-SEQ ID NO: 31-5' |
| 32 | 1 | 5'-UUG$_1$CUG$_1$AG$_1$CUU-3' | 5'-SEQ ID NO: 1-3' |
| 33 | 2 | 5'-UG$_1$AUG$_1$ACG$_1$AUU-3' | 5'-SEQ ID NO: 2-3' |
| 34 | 3 | 5'-UG$_1$ACG$_1$AUG$_1$AUU-3' | 5'-SEQ ID NO: 3-3' |
| 35 | 4 | 5'-CUUG$_1$UG$_1$AG$_1$CUU-3' | 5'-SEQ ID NO: 4-3' |
| 36 | 5 | 5'-CUG$_1$AG$_1$AAG$_1$CUU-3' | 5'-SEQ ID NO: 5-3' |
| 37 | 6 | 5'-CUG$_1$ACG$_1$AG$_1$CUU-3' | 5'-SEQ ID NO: 6-3' |
| 38 | 7 | 5'-ACUUG$_1$ACUUG$_1$A-3' | 5'-SEQ ID NO: 7-3' |
| 39 | 8 | 5'-ACUUG$_1$ACG$_1$AUU-3' | 5'-SEQ ID NO: 8-3' |
| 40 | 9 | 5'-ACUUG$_1$ACCUUU-3' | 5'-SEQ ID NO: 9-3' |
| 41 | 10 | 5'-ACUUG$_1$ACCUG$_1$U-3' | 5'-SEQ ID NO: 10-3' |
| 42 | 11 | 5'-ACUUG$_1$AAG$_1$CUU-3' | 5'-SEQ ID NO: 11-3' |
| 43 | 12 | 5'-ACUUG$_1$AACUUG$_1$-3' | 5'-SEQ ID NO: 12-3' |
| 44 | 13 | 5'-ACUUG$_1$AAACCU-3' | 5'-SEQ ID NO: 13-3' |
| 45 | 14 | 5'-ACUG$_1$CG$_1$AG$_1$CUU-3' | 5'-SEQ ID NO: 14-3' |

TABLE 4-continued

Stabilized RNA-based Immune Modulatory Oligonucleotide (SIMRA) Sequences

| SIMRA# | SEQ ID NO: | Sequences and Modification | SIMRA Structure |
|---|---|---|---|
| 46 | 15 | 5'-ACUG$_l$AG$_l$AG$_l$CUU-3' | 5'-SEQ ID NO: 15-3' |
| 47 | 16 | 5'-ACG$_l$UG$_l$AAG$_l$CUU-3' | 5'-SEQ ID NO: 16-3' |
| 48 | 17 | 5'-ACG$_l$CUG$_l$AG$_l$CUU-3' | 5'-SEQ ID NO: 17-3' |
| 49 | 18 | 5'-AAUUG$_l$ACG$_l$CUU-3' | 5'-SEQ ID NO: 18-3' |
| 50 | 19 | 5'-AAUUG$_l$ACG$_l$CUG$_l$-3' | 5'-SEQ ID NO: 19-3' |
| 51 | 20 | 5'-AAG$_l$UG$_l$CG$_l$ACUU-3' | 5'-SEQ ID NO: 20-3' |
| 52 | 21 | 5'-AAG$_l$UG$_l$ACG$_l$CUU-3' | 5'-SEQ ID NO: 21-3' |
| 53 | 22 | 5'-AAG$_l$UG$_l$ACG$_l$AUU-3' | 5'-SEQ ID NO: 22-3' |
| 54 | 23 | 5'-AACUUG$_l$AG$_l$CUU-3' | 5'-SEQ ID NO: 23-3' |
| 55 | 24 | 5'-AACUG$_l$CG$_l$ACUU-3' | 5'-SEQ ID NO: 24-3' |
| 56 | 25 | 5'-AACUG$_l$ACG$_l$CUU-3' | 5'-SEQ ID NO: 25-3' |
| 57 | 26 | 5'-AACUG$_l$ACG$_l$CUG$_l$-3' | 5'-SEQ ID NO: 26-3' |
| 58 | 27 | 5'-UG$_l$AUG$_l$AAG$_l$CUU-3' | 5'-SEQ ID NO: 27-3' |
| 59 | 28 | 5'-AACUG$_l$AAG$_l$CUU-3' | 5'-SEQ ID NO: 28-3' |
| 60 | 29 | 5'-AACUG$_l$AAG$_l$CUG$_l$-3' | 5'-SEQ ID NO: 29-3' |
| 61 | 30 | 5'-AAUUG$_l$AAG$_l$CUU-3' | 5'-SEQ ID NO: 30-3' |
| 62 | 31 | 5'-AAUUG$_l$AAG$_l$CUG$_l$-3' | 5'-SEQ ID NO: 31-3' |

$G_l$ = 7-deaza-G; X = 1,2,3-propanetriol

In a second aspect, the invention provides pharmaceutical formulations comprising a TLR7-specific SIMRA compound according to the invention and a pharmaceutically acceptable carrier.

In a third aspect, the invention provides methods for generating TLR7 mediated immune responses in a vertebrate, such methods comprising administering to the vertebrate a TLR7-specific SIMRA compound according to the invention. In some embodiments, the vertebrate is a mammal. In preferred embodiments, the TLR7-specific SIMRA compound according to the invention is administered to a vertebrate in need of immune modulation.

In a fourth aspect, the invention provides methods for therapeutically treating a patient having a disease or disorder, such methods comprising administering to the patient a TLR7-specific SIMRA compound according to the invention. In various embodiments, the disease or disorder to be treated is one in which an immune modulation may be desirable, including but not limited to cancer, an autoimmune disorder, infectious disease, airway inflammation, inflammatory disorders, allergy, asthma, or a disease caused by a pathogen. Pathogens include bacteria, parasites, fungi, viruses, viroids, and prions.

In a fifth aspect, the invention provides methods for preventing a disease or disorder, such methods comprising administering to the patient a TLR7-specific SIMRA compound according to the invention. In various embodiments, the disease or disorder to be prevented is one in which an immune modulation may be desirable, including but not limited to cancer, an autoimmune disorder, airway inflammation, inflammatory disorders, infectious disease, allergy, asthma, or a disease caused by a pathogen. Pathogens include bacteria, parasites, fungi, viruses, viroids, and prions.

In a sixth aspect, the invention provides a method of preventing or treating a disorder, such methods comprising isolating cells capable of producing cytokines or chemokines (including, but not limited to, immune cells, B cells, T-regulatory cells, B-cells, PBMCs, pDCs and lymphoid cells), culturing such cells under standard cell culture conditions, treating such cells ex vivo with a TLR7-specific SIMRA such that the isolated cells produce or secrete increased levels of cytokines or chemokines, and administering or re-administering the treated cells to a patient in need of cytokine or chemokine therapy for the prevention or treatment of disease. This aspect of the invention would be in accordance with standard adoptive cellular immunotherapy techniques to produce activated immune cells.

In some embodiments of this aspect of the invention, the cells capable of producing cytokines or chemokines may be isolated from subjects with or without a disease or disorder. Such isolation may include identification and selection and could be performed using standard cell isolation procedures, including those set forth in the specific examples below. Such isolated cells are cultured according to standard cell culturing procedures and using standard cell culture conditions, which may include the culturing procedures and conditions set forth in the specific examples below. In a further aspect of this embodiment of the invention, the isolated cells are cultured in the presence of at least one TLR7-specific SIMRA according to the invention, in an amount and for a time period sufficient to induce, increase, or enhance the production and/or secretion of cytokines and/or chemokines as compared to the isolated cells cultured in the absence of such one or more TLR7-specific SIMRA according to the invention. Such time may be from seconds, to minutes, to hours, to days. Such isolated, TLR7-specific SIMRA-treated cells may find use following re-administration to the donor or administration to a second histologically compatible patient, wherein such donor or second patient are in need of induced, increased or enhanced production and/or secretion of cytokines and/or chemokines. For example, re-administration to a donor or administration to a second patient having cancer, an autoimmune disorder, airway inflammation, inflammatory disorders, infectious disease, allergy, asthma or a disease caused by a pathogen. Such re-administration or administration may be accomplished using various modes, including catheter or injection administration or any other effective route. This aspect of the invention may also find use in patients who may have a limited or incomplete ability to mount an immune response or are immune compromised (e.g., patient infected with HIV and bone marrow transplant patients). This aspect of the invention may also find use in combination with administering TLR7-specific SIMRA according to the invention to the patient administered or re-administered the isolated, TLR7-specific SIMRA-treated cells.

In any of the methods according to the invention, the TLR7-specific SIMRA compound of the invention can variously act by producing direct immune modulatory effects alone or in combination with any other agent useful for treating or preventing the disease or condition that does not abolish the immune modulatory effect of the TLR7-specific SIMRA compound. In any of the methods according to the invention, the agent(s) useful for treating or preventing the disease or condition includes, but is not limited to, vaccines, antigens, antibodies, preferably monoclonal antibodies, cytotoxic agents, allergens, antibiotics, siRNA, microRNA, antisense oligonucleotides, TLR agonist (e.g., agonists of TLR9 and/or agonists of TLR7 and/or agonists of TLR8), chemotherapeutic agents (both traditional chemotherapy and modern targeted therapies), targeted therapeutic agents, activated cells, peptides, proteins, gene therapy vectors, peptide vaccines, protein vaccines, DNA vaccines, adjuvants, and co-stimulatory molecules (e.g., cytokines, chemokines, protein ligands, trans-activating factors, peptides or peptides comprising modified amino acids), or combinations thereof. For example, in the treatment of cancer, it is contemplated that the TLR7-specific SIMRA compound according to the invention may be administered in combination with one or more chemotherapeutic compound, targeted therapeutic agent and/or monoclonal antibody. Alternatively, the agent can include DNA vectors encoding for antigen or allergen. Alternatively, the TLR7-specific SIMRA compounds according to the invention can be administered in combination with other adjuvants to enhance the specificity or magnitude of the immune response to the TLR7-specific SIMRA compound.

In any of the methods according to the invention, administration of TLR7-specific SIMRA compounds according to the invention, alone or in combination with any other agent, can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch, or in eye drop or mouthwash form. Administration of the therapeutic compositions of TLR7-specific SIMRA compounds according to the invention can be carried out using known procedures using a pharmaceutically effective amount and for periods of time effective to reduce symptoms or surrogate markers of the disease. For example, a pharmaceutically effective amount of a TLR7-specific SIMRA compound according to the invention for treating a disease and/or disorder could be that amount necessary to alleviate or reduce the symptoms, or delay or ameliorate a tumor, cancer, or bacterial, viral, or fungal infection. A pharmaceutically effective amount for use as a vaccine adjuvant could be that amount useful for boosting a subject's immune response to a vaccine or antigen. In the context of administering a composition that modulates an immune response to a co-administered antigen, a pharmaceutically effective amount of a TLR7-specific SIMRA compound according to the invention and antigen is an amount sufficient to achieve the desired modulation as compared to the immune response obtained when the antigen is administered alone. The effective amount for any particular application can vary depending on such factors as the disease or condition being treated, the particular oligonucleotide being administered, the size of the subject or the severity of the disease or condition. One of ordinary skill in the art can empirically determine the pharmaceutically effective amount of a particular oligonucleotide without necessitating undue experimentation.

When administered systemically, the therapeutic composition is preferably administered at a sufficient dosage to attain a blood level of TLR7-specific SIMRA compound according to the invention from about 0.0001 micromolar to about 10 micromolar. For localized administration, much lower concentrations than this may be effective, and much higher concentrations may be tolerated. Preferably, a total dosage of TLR7-specific SIMRA compound according to the invention ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The TLR7-specific SIMRA compound according to the invention may optionally be linked to one or more allergens and/or antigens (self or foreign), an immunogenic protein or peptide, such as keyhole limpet hemocyanin (KLH), cholera toxin B subunit, or any other immunogenic carrier protein. TLR7-specific SIMRA compounds according to the invention can also be used in combination with other compounds (e.g., adjuvants) including, without limitation, TLR agonists (e.g., agonist of TLR2, TLR3, TLR4, TLR5, TLR6, TLR7, TLR8, and/or TLR9), Freund's incomplete adjuvant, KLH, monophosphoryl lipid A (MPL), alum, and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric, adult, and veterinary vaccine applications.

The examples below are intended to further illustrate certain exemplary embodiments of the invention, and are not intended to limit the scope of the invention.

EXAMPLES

Example 1

Immune Modulatory Oligoribonucleotide Synthesis

The immune modulatory oligoribonucleotides were chemically synthesized using phosphoramidite chemistry on automated DNA/RNA synthesizer. N-acetyl protected (Except U) 2'-O-TBDMS RNA monomers, A, G, C, and U, were purchased from Sigma-Aldrich. 7-deaza-G, inosine was purchased from ChemGenes Corporation. 0.25M 5-ethylthio-1H-tetrazole, PAC-anhydride Cap A and Cap B were purchased from Glen Research. 3% trichloroacetic acid (TCA) in dichloromethane (DCM) and 5% 3H-1,2-Benzodithiole-3-one-1,1-dioxide (Beaucage reagent) were made in house.

Immune modulatory oligoribonucleotides were synthesized at 1-2 μM scale using a standard RNA synthesis protocol.

Cleavage and Base Deprotection

Immune modulatory oligoribonucleotides were cleaved from solid support and the protecting groups of exo-cyclic-amines were removed in methylamine and ammonium hydroxide solution. The resulting solution was dried completely in a SpeedVac.

IE HPLC Purification

Immune modulatory oligoribonucleotides were purified by ion exchange HPLC. Using Dionex DNAPac 100 column. Crude immune modulatory oligoribonucleotide solution was injected into HPLC. Above gradient is performed and the fractions were collected. All fractions containing more than 90% desired product were mixed, and then the solution was concentrated to almost dry by RotoVap. RNAse-free water was added to make final volume of 10 ml.

C-18 Reversed Phase Desalting

A C-18 Sep-Pak cartridge purchased from Waters was washed by passing with 10 ml of acetonitrile followed by 10 ml of 0.5 M sodium acetate through the cartridge. Then 10 ml of immune modulatory oligoribonucleotide solution was loaded on to the cartridge. Then 15 ml of water was used to wash out the salt. The immune modulatory oligoribonucleotide was finally eluted using 1 ml of 50% acetonitrile in water. The solution was placed in SpeedVac for 30 minutes. The remaining solution was filtered through a 0.2 micron filter and then was lyophilized. The solid was then re-dissolved in RNAse free water to make the desired concentration. The final solution was stored below 0° C. Oligoribonucleotides were analyzed for purity by Capillary Electrophoresis, Ion Exchange HPLC, and PAGE analysis, and for molecular mass by MALDI-ToF mass spectrometry.

Example 2

Protocols for Assays with HEK293 Cells Expressing TLRs

HEK293 or HEK293XL/human TLR7 or HEK293 or HEK293XL/human TLR8 cells (InvivoGen, San Diego, Calif.) were cultured in 48-well plates in 250 μl/well DMEM supplemented with 10% heat-inactivated FBS in a 5% $CO_2$ incubator.

Reporter Gene Transformation

HEK293 or HEK293XL cells stably expressing human TLR7 or TLR8 (InvivoGen, San Diego, Calif.) were cultured in 48-well plates in 250 μl/well DMEM supplemented with 10% heat-inactivated FBS in a 5% $CO_2$ incubator. At 80% confluence, cultures were transiently transfected with 400 ng/ml of SEAP (secreted form of human embryonic alkaline phosphatase) reporter plasmid (pNifty2-Seap) (Invivogen) in the presence of 4 μl/ml of lipofectamine (Invitrogen, Carlsbad, Calif.) in culture medium. Plasmid DNA and lipofectamine were diluted separately in serum-free medium and incubated at room temperature for 5 minutes. After incubation, the diluted DNA and lipofectamine were mixed and the mixtures were incubated at room temperature for 20 minutes. Aliquots of 25 μl of the DNA/lipofectamine mixture containing 100 ng of plasmid DNA and 1 μl of lipofectamine were added to each well of the cell culture plate, and the cultures were continued for 4 hours.

IMO-Treatment

After transfection, medium was replaced with fresh culture medium. The HEK293 or HEK29XL cells expressing human TLR7 or TLR8 were stimulated with 50 μg/ml of TLR7-specific SIMRAs according to the invention or PBS control and the cultures were continued for 18 to 20 hours. At the end of TLR7-specific SIMRA treatment, 30 μl of culture supernatant was taken from each treatment and used for SEAP assay following manufacturer's protocol (InvivoGen).

SEAP (Secreted Form of Human Embryonic Alkaline Phosphatase) Assay

Briefly, culture supernatants were incubated with p-nitrophynyl phosphate substrate and the yellow color generated was measured by a plate reader at 405 nm.

TLR7 and TLR8 activity in HEK293 cells expressing human TLR7 and TLR8 is shown in Table 5. The data shown in Table 5 was generated by stimulating HEK293 cells with 50 μg/ml of TLR7-specific SIMRA according to the invention for 18 hours, and determining the levels of NF-κB using SEAP (secreted form of human embryonic alkaline phosphatase) assay. The data are shown as fold increase in NF-κB activity over PBS control. (Putta, M. R. et al. (2006) *Nucleic Acids Res.* 34:3231-38). The data shown in Table 5 demonstrate that administration of a TLR7-specific SIMRA according to the invention generates a distinct and specific TLR7-mediated immune response profile.

TABLE 5

TLR 7 and 8 Activation by TLR7-Specific SIMRA Compounds

| SEQ ID NO: | Sequence | TLR7 at 50 mg/ml | TLR8 at 50 mg/ml | TLR7/ TLR8 Activity |
|---|---|---|---|---|
| PBS | | 1 | 1 | 1 |
| 1 | 5'-UUG$_1$CUG$_1$AG$_1$CUU-X-UUCG$_1$AUCG$_1$UU-5' | 11.79 | 0.38 | 31.03 |
| 2 | 5'-UG$_1$AUG$_1$ACG$_1$AUU-X-UUAG$_1$CAG$_1$UAG$_1$U-5' | 19.68 | 2.60 | 7.57 |
| 3 | 5'-UG$_1$ACG$_1$AUG$_1$AUU-X-UUAG$_1$UAG$_1$CAG$_1$U-5' | 18.35 | 4.60 | 3.99 |
| 4 | 5'-CUUG$_1$UG$_1$AG$_1$CUU-X-UUCG$_1$AG$_1$UG$_1$UUC-5' | 16.65 | 1.50 | 11.10 |

TABLE 5-continued

TLR 7 and 8 Activation by TLR7-Specific SIMRA Compounds

| SEQ ID NO: | Sequence | TLR7 at 50 mg/ml | TLR8 at 50 mg/ml | TLR7/ TLR8 Activity |
|---|---|---|---|---|
| 5 | 5'-CUG$_1$AG$_1$AAG$_1$CUU-X-UUCG$_1$AAG$_1$AG$_1$UC-5' | 17.98 | 0.38 | 47.32 |
| 6 | 5'-CUG$_1$ACG$_1$AG$_1$CUU-X-UUCG$_1$AG$_1$CAG$_1$UC-5' | 15.23 | 0.55 | 27.69 |
| 7 | 5'-ACUUG$_1$ACUUG$_1$A-X-AG$_1$UUCAG$_1$UUCA-5' | 10.47 | 1.40 | 7.48 |
| 8 | 5'-ACUUG$_1$ACG$_1$AUU-X-UUAG$_1$CAG$_1$UUCA-5' | 16.58 | 2.05 | 8.09 |
| 9 | 5'-ACUUG$_1$ACCUUU-X-UUUCCAG$_1$UUCA-5' | 8.26 | 1.77 | 4.67 |
| 10 | 5'-ACUUG$_1$ACCUG$_1$U-X-UG$_1$UCCAG$_1$UUCA-5' | 6.08 | 0.73 | 8.33 |
| 11 | 5'-ACUUG$_1$AAG$_1$CUU-X-UUCG$_1$AAG$_1$UUCA-5' | 30.77 | 3.02 | 10.19 |
| 12 | 5'-ACUUG$_1$AACUUG$_1$-X-G$_1$UUCAAG$_1$UUCA-5' | 14.71 | 4.85 | 3.03 |
| 13 | 5'-ACUUG$_1$AAACCU-X-UCCAAAG$_1$UUCA-5' | 17.64 | 1.40 | 12.60 |
| 14 | 5'-ACUG$_1$CG$_1$AG$_1$CUU-X-UUCG$_1$AG$_1$CG$_1$UCA-5' | 14.06 | 2.68 | 5.25 |
| 15 | 5'-ACUG$_1$AG$_1$AG$_1$CUU-X-UUCG$_1$AG$_1$AG$_1$UCA-5' | 16.77 | 0.60 | 27.95 |
| 16 | 5'-ACG$_1$UG$_1$AAG$_1$CUU-X-UUCG$_1$AAG$_1$UG$_1$CA-5' | 12.17 | 1.95 | 6.24 |
| 17 | 5'-ACG$_1$CUG$_1$AG$_1$CUU-X-UUCG$_1$AG$_1$UCG$_1$CA-5' | 14.31 | 0.88 | 16.26 |
| 18 | 5'-AAUUG$_1$ACG$_1$CUU-X-UUCG$_1$CAG$_1$UUAA-5' | 10.35 | 0.25 | 41.40 |
| 19 | 5'-AAUUG$_1$ACG$_1$CUG$_1$-X-G$_1$UCG$_1$CAG$_1$UUAA-5' | 11.94 | 0.20 | 59.70 |
| 20 | 5'-AAG$_1$UG$_1$CG$_1$ACUU-X-UUCAG$_1$CG$_1$UG$_1$AA-5' | 9.81 | 0.53 | 18.51 |
| 21 | 5'-AAG$_1$UG$_1$ACG$_1$CUU-X-UUCG$_1$CAG$_1$UG$_1$AA-5' | 12.94 | 0.65 | 19.91 |
| 22 | 5'-AAG$_1$UG$_1$ACG$_1$AUU-X-UUAG$_1$CAG$_1$UG$_1$AA-5' | 8.13 | 0.75 | 10.84 |
| 23 | 5'-AACUUG$_1$AG$_1$CUU-X-UUCAG$_1$AG$_1$UUCAA-5' | 8.85 | 1.03 | 8.59 |
| 24 | 5'-AACUG$_1$CG$_1$ACUU-X-UUCAG$_1$CG$_1$UCAA-5' | 6.54 | 0.30 | 21.80 |
| 25 | 5'-AACUG$_1$ACG$_1$CUU-X-UUCG$_1$CAG$_1$UCAA-5' | 10.54 | 0.40 | 26.35 |
| 26 | 5'-AACUG$_1$ACG$_1$CUG$_1$-X-G$_1$UCG$_1$CAG$_1$UCAA-5' | 8.73 | 0.43 | 20.30 |
| 27 | 5'-UG$_1$AUG$_1$AAG$_1$CUU-X-UUCG$_1$AAG$_1$UAG$_1$U-5' | 15.85 | 0.60 | 26.42 |
| 28 | 5'-AACUG$_1$AAG$_1$CUU-X-UUCG$_1$AAG$_1$UCAA-5' | 27.32 | 1.02 | 26.78 |
| 29 | 5'-AACUG$_1$AAG$_1$CUG$_1$-X-G$_1$UCG$_1$AAG$_1$UCAA-5' | 13.70 | 0.58 | 23.62 |
| 30 | 5'-AAUUG$_1$AAG$_1$CUU-X-UUCG$_1$AAG$_1$UUAA-5' | 22.67 | 1.57 | 14.44 |
| 31 | 5'-AAUUG$_1$AAG$_1$CUG$_1$-X-G$_1$UCG$_1$AAG$_1$UUAA-5' | 9.80 | 0.73 | 13.42 |

G$_1$ = 7-deaza-G; X = 1,2,3-propanediol (glycerol)

Example 3

Human Cell Culture Protocols

Human PBMC Isolation

Peripheral blood mononuclear cells (PBMCs) from freshly drawn, healthy volunteer blood (CBR Laboratories, Boston, Mass.) were isolated by Ficoll density gradient centrifugation method (Histopaque-1077, Sigma).

Human pDC Isolation

Peripheral blood mononuclear cells (PBMCs) from freshly drawn healthy volunteer blood (CBR Laboratories, Boston, Mass.) can be isolated by Ficoll density gradient centrifugation method (Histopaque-1077, Sigma). pDCs can be isolated from PBMCs by positive selection using the BDCA4 cell isolation kits (Miltenyi Biotec) according to the manufacturer's instructions.

Human mDC Isolation

Peripheral blood mononuclear cells (PBMCs) from freshly drawn healthy volunteer blood (CBR Laboratories, Boston, Mass.) can be isolated by Ficoll density gradient centrifugation method (Histopaque-1077, Sigma). Myeloid dendritic cells (mDCs) can be isolated from PBMCs by positive selection using the BDCA4 cell isolation kits (Miltenyi Biotec) according to the manufacturer's instructions.

Multiplex Cytokine Assays

Human PBMCs were plated in 48-well plates using 5×10$^6$ cells/ml. pDCs can be plated in 96-well dishes using 1×10$^6$ cells/ml. The TLR7-specific SIMRA compounds according to the invention dissolved in DPBS (pH 7.4; Mediatech) were added to a final concentration of 50 or 100 μg/ml in the cell cultures. The cells were then incubated at 37° C. for 24 hours and the supernatants collected for luminex multiplex or ELISA assays. The experiments were performed in triplicate wells. The levels of IFN-α, IL-6, or TNF-α were measured by sandwich ELISA. The required reagents, including cytokine antibodies and standards, were purchased from PharMingen.

Luminex multiplex assays were performed using Biosource human multiplex cytokine assay kits on Luminex 100/200 instrument and the data were analyzed using StarStation software supplied by Applied Cytometry Systems (Sacramento, Calif.).

Cytokine concentrations from human PBMCs are shown in Table 6. The data shown in Table 6 was generated by isolating PBMCs from freshly obtained healthy human volunteer's blood and culturing with 100 μg/ml dose of TLR7-specific SIMRA for 24 hours; supernatants were collected and analyzed by Luminex multiplex assay for cytokine concentrations. The results shown in Table 6 demonstrate that administration of TLR7-specific SIMRA oligonucleotides according to the invention generates unique cytokine and chemokine profiles.

TABLE 6

Cytokine/Chemokines Induced by TLR7-Specific SIMRA Compounds in Human PBMC

| SEQ ID NO | Sequence | IFN-α at 100 mg/ml (pg/ml) | TNF-α at 100 mg/ml (pg/ml) | IL-12 at 100 mg/ml (pg/ml) |
|---|---|---|---|---|
| DPBS | | 0 | 0 | 0 |
| 1 | 5'-UUG$_1$CUG$_1$AG$_1$CUU-X-UUCG$_1$AUCG$_1$UU-5' | 145.01 | 415.30 | 1366.0 |
| 2 | 5'-UG$_1$AUG$_1$ACG$_1$AUU-X-UUAG$_1$CAG$_1$UAG$_1$U-5' | 182.74* | — | 102.10* |
| 3 | 5'-UG$_1$ACG$_1$AUG$_1$AUU-X-UUAG$_1$UAG$_1$CAG$_1$U-5' | 258.94* | — | 221.40* |
| 4 | 5'-CUUG$_1$UG$_1$AG$_1$CUU-X-UUCG$_1$AG$_1$UG$_1$UUC-5' | 138.13 | 403.13 | 1020.8 |
| 5 | 5'-CUG$_1$AG$_1$AAG$_1$CUU-X-UUCG$_1$AAG$_1$AG$_1$UC-5' | 123.12 | 818.21 | 1748.3 |
| 6 | 5'-CUG$_1$ACG$_1$AG$_1$CUU-X-UUCG$_1$AG$_1$CAG$_1$UC-5' | 106.43 | 63.25 | 518.79 |
| 7 | 5'-ACUUG$_1$ACUUG$_1$A-X-AG$_1$UUCAG$_1$UUCA-5' | 95.41 * | 205.92* | 640.47* |
| 8 | 5'-ACUUG$_1$ACG$_1$AUU-X-UUAG$_1$CAG$_1$UUCA-5' | 232.84* | 20.86* | 393.68* |
| 9 | 5'-ACUUG$_1$ACCUUU-X-UUUCCAG$_1$UUCA-5' | 95.41 | 83.56 | 306.94 |
| 10 | 5'-ACUUG$_1$ACCUG$_1$U-X-UG$_1$UCCAG$_1$UUCA-5' | 101.46 | 29.27 | 469.64 |
| 11 | 5'-ACUUG$_1$AAG$_1$CUU-X-UUCG$_1$AAG$_1$UUCA-5' | 217.55* | 3594* | 442.09* |
| 12 | 5'-ACUUG$_1$AACUUG$_1$-X-G$_1$UUCAAG$_1$UUCA-5' | 96.82 | 33.44 | 417.12 |
| 13 | 5'-ACUUG$_1$AAACCU-X-UCCAAAG$_1$UUCA-5' | 12.23 | 9.35 | 76.89 |
| 14 | 5'-ACUG$_1$CG$_1$AG$_1$CUU-X-UUCG$_1$AG$_1$CG$_1$UCA-5' | 130.63 | 43.48 | 487.23 |
| 15 | 5'-ACUG$_1$AG$_1$AG$_1$CUU-X-UUCG$_1$AG$_1$AG$_1$UCA-5' | 145.01 | 1081.7 | 1472.9 |
| 16 | 5'-ACG$_1$UG$_1$AAG$_1$CUU-X-UUCG$_1$AAG$_1$UG$_1$CA-5' | 123.12 | 164.68 | 864.20 |
| 17 | 5'-ACG$_1$CUG$_1$AG$_1$CUU-X-UUCG$_1$AG$_1$UCG$_1$CA-5' | 187.88 | 1407.0 | 2237.4 |
| 18 | 5'-AAUUG$_1$ACG$_1$CUU-X-UUCG$_1$CAG$_1$UUAA-5' | 192.68 | 8.80 | 340.36 |
| 19 | 5'-AAUUG$_1$ACG$_1$CUG$_1$-X-G$_1$UCG$_1$CAG$_1$UUAA-5' | — | 5.24 | 323.59 |
| 20 | 5'-AAG$_1$UG$_1$CG$_1$ACUU-X-UUCAG$_1$CG$_1$UG$_1$AA-5' | 123.12 | 1.73 | 170.61 |
| 21 | 5'-AAG$_1$UG$_1$ACG$_1$CUU-X-UUCG$_1$CAG$_1$UG$_1$AA-5' | 204.22 | 26.18 | 352.06 |
| 22 | 5'-AAG$_1$UG$_1$ACG$_1$AUU-X-UUAG$_1$CAG$_1$UG$_1$AA-5' | 253.89 | 15.74 | 400.40 |
| 23 | 5'-AACUUG$_1$AG$_1$CUU-X-UUCAG$_1$AG$_1$UUCAA-5' | 106.43 | 74.41 | 527.01 |
| 24 | 5'-AACUG$_1$CG$_1$ACUU-X-UUCAG$_1$CG$_1$UCAA-5' | 151.42 | 1.73 | 181.45 |
| 25 | 5'-AACUG$_1$ACG$_1$CUU-X-UUCG$_1$CAG$_1$UCAA-5' | 292.47 | 20.28 | 249.79 |
| 26 | 5'-AACUG$_1$ACG$_1$CUG$_1$-X-G$_1$UCG$_1$CAG$_1$UCAA-5' | — | −153.46 | |
| 27 | 5'-UG$_1$AUG$_1$AAG$_1$CUU-X-UUCG$_1$AAG$_1$UAG$_1$U-5' | 141.80 | 254.96 | 863.40 |

$G_1$ = 7-deaza-G; X = 1,2,3-propanediol (glycerol)
* Data 50 μg/ml concentration

Example 4

In Vivo Cytokine Secretion in Mouse Model Treated with TLR7 Agonist Compounds C57BL/6 mice, 5-6 weeks old, were obtained from Taconic Farms, Germantown, N.Y., and maintained in accordance with Idera Pharmaceutical's IACUC approved animal protocols. Mice (n=3) were injected subcutaneously (s.c.) with individual TLR7-specific SIMRA compounds according to the invention at 25 mg/kg (single dose). Serum was collected by retro-orbital bleeding 2 hours after TLR7-specific SIMRA administration and cytokine and chemokine levels were determined by sandwich ELISA or Luminex multiplex assays. The results are shown in Table 7 and demonstrate that in vivo administration of TLR7-specific SIMRA oligonucleotides according to the invention generates unique cytokine and chemokine profiles. All reagents, including cytokine and chemokine antibodies and standards were purchased from PharMingen. (San Diego, Calif.).

TABLE 7

IL-12 induced by TLR7-specific SIMRA compounds in vivo in mice at dosage of 25 mg/kg

| SEQ ID NO: | Sequence | IL-12 ± SD (pg/ml) |
|---|---|---|
|  | Control | 0 ± 0.0 |
| 2 | 5'-UG$_1$AUG$_1$ACG$_1$AUU-X-UUAG$_1$CAG$_1$UAG$_1$U-5' | 49624.3 ± 6892.4 |
| 5 | 5'-CUG$_1$AG$_1$AAG$_1$CUU-X-UUCG$_1$AAG$_1$AG$_1$UC-5' | 198743.8 ± 38745.3 |
| 8 | 5'-ACUUG$_1$ACG$_1$AUU-X-UUAG$_1$CAG$_1$IUCA-5' | 121683.4 ± 13046.7 |
| 11 | 5'-ACUUG$_1$AAG$_1$CUU-X-UUCG$_1$AAGdJUCA-5' | 124658.0 ± 12493.8 |
| 14 | 5'-ACUG$_1$CG$_1$AG$_1$CUU-X-UUCG$_1$AG$_1$CG$_1$UCA-5' | 159013.9 ± 16081.0 |
| 18 | 5'-AAUUG$_1$ACG$_1$CUU-X-UUCG$_1$CAG$_1$UUAA-5' | 107053.8 ± 9766.2 |
| 22 | 5'-AAG$_1$UG$_1$ACG$_1$AUU-X-UUAG$_1$CAG$_1$UG$_1$AA-5' | 41640.7 ± 1773.0 |

$G_1$ = 7-deaza-G; X = 1,2,3-propanediol (glycerol)

Example 5

Serum Stability Assay

Approximately 0.5 OD of exemplary TLR7-specific SIMRA compounds according to the invention would be individually incubated in 1% human serum in PBS for 30 minutes at 37° C. Following 30 minutes of incubation in 1% human serum, the TLR7-specific SIMRA compound would be analyzed on anion-exchange HPLC to determine the percentage of full-length TLR7-specific SIMRA compound that remained as compared to the amount of TLR7-specific SIMRA compound present before serum treatment. The results are expected to demonstrate that chemical modifications according to the invention made to RNA-based compounds can enhance their stability.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed:

1. A stabilized immune modulatory RNA (SIMRA) compound having the sequence:
   (a) 5'-UUG$_1$CUG$_1$AG$_1$CUU-X-UUCG$_1$AG$_1$UCG$_1$UU-5' (5'-SEQ ID NO:1-3'-X-3'-SEQ ID NO:1-5');
   (b) 5'-CUG$_1$AG$_1$AAG$_1$CUU-X-UUCG$_1$AAG$_1$AG$_1$UC-5' (5'-SEQ ID NO:5-3'-X-3'-SEQ ID NO:5-5');
   (c) 5'-CUG$_1$ACG$_1$AG$_1$CUU-X-UUCG$_1$AG$_1$CAG$_1$UC-5' (5'-SEQ ID NO:6-3'-X-3'-SEQ ID NO:6-5');
   (d) 5'-ACUUG$_1$ACCUG$_1$U-X-UG$_1$UCCAG$_1$UUCA-5' (5'-SEQ ID NO:10-3'-X-3'-SEQ ID NO:10-5');
   (e) 5'-ACUG$_1$AG$_1$AG$_1$CUU-X-UUCG$_1$AG$_1$AG$_1$UCA-5' (5'-SEQ ID NO:15-3'-X-3'-SEQ ID NO:15-5');
   (f) 5'-ACG$_1$CUG$_1$AG$_1$CUU-X-UUCG$_1$AG$_1$UCG$_1$CA-5' (5'-SEQ ID NO:17-3'-X-3'-SEQ ID NO:17-5');
   (g) 5'-AAUUG$_1$ACG$_1$CUU-X-UUCG$_1$CAG$_1$UUAA-5' (5'-SEQ ID NO:18-3'-X-3'-SEQ ID NO:18-5');
   (h) 5'-AAUUG$_1$ACG$_1$CUG$_1$-X-G$_1$UCG$_1$CAG$_1$UUAA-5' (5'-SEQ ID NO:19-3'-X-3'-SEQ ID NO:19-5');
   (i) 5'-AAG$_1$UG$_1$CG$_1$ACUU-X-UUCAG$_1$CG$_1$UG$_1$AA-5' (5'-SEQ ID NO:20-3'-X-3'-SEQ ID NO:20-5');
   (j) 5'-AAG$_1$UG$_1$ACG$_1$CUU-X-UUCG$_1$CAG$_1$UG$_1$AA-5' (5'-SEQ ID NO:21-3'-X-3'-SEQ ID NO:21-5');
   (k) 5'-AAG$_1$UG$_1$ACG$_1$AUU-X-UUAG$_1$CAG$_1$UG$_1$AA-5' (5'-SEQ ID NO:22-3'-X-3'-SEQ ID NO:22-5');
   (l) 5'-AACUUG$_1$AG$_1$CUU-X-UUCG$_1$AG$_1$UUCAA-5' (5'-SEQ ID NO:23-3'-X-3'-SEQ ID NO:23-5');
   (m) 5'-AACUG$_1$CG$_1$ACUU-X-UUCAG$_1$CG$_1$UCAA-5' (5'-SEQ ID NO:24-3'-X-3'-SEQ ID NO:24-5');
   (n) 5'-AACUG$_1$ACG$_1$CUU-X-UUCG$_1$CAG$_1$UCAA-5' (5'-SEQ ID NO:25-3'-X-3'-SEQ ID NO:25-5');
   (o) 5'-AACUG$_1$ACG$_1$CUG$_1$-X-G$_1$UCG$_1$CAG$_1$UCAA-5' (5'-SEQ ID NO:26-3'-X-3'-SEQ ID NO:26-5');
   (p) 5'-AACUG$_1$AAG$_1$CUU-X-UUCG$_1$AAG$_1$UCAA-5' (5'-SEQ ID NO:28-3'-X-3'-SEQ ID NO:28-5');
   (q) 5'-AACUG$_1$AAG$_1$CUG$_1$-X-G$_1$UCG$_1$AAG$_1$UCAA-5' (5'-SEQ ID NO:29-3'-X-3'-SEQ ID NO:29-5'); or
   (r) 5'-AAUUG$_1$AAG$_1$CUG$_1$-X-G$_1$UCG$_1$AAG$_1$UUAA-5' (5'-SEQ ID NO:31-3'-X-3'-SEQ ID NO:31-5');
   wherein G$_1$ is 7-deaza-G and X is a glycerol linker, and wherein the compound selectively induces activity through TLR7.

2. A composition comprising the SIMRA compound of claim 1 and a physiologically acceptable carrier.

3. A method for generating a TLR7-mediated immune response in an individual, the method comprising administering to the individual the SIMRA compound according to claim 1.

* * * * *